United States Patent [19]
Fujii et al.

[11] Patent Number: 5,616,556
[45] Date of Patent: Apr. 1, 1997

[54] METHOD OF TREATING RHEUMATOID ARTHRITIS AND OSTEOARTHROSIS USING TETRAHYDRO WS9326A

[75] Inventors: Takashi Fujii, Ikeda; Masaaki Tomoi, Higashiosaka, both of Japan

[73] Assignee: Fujisawa Pharmaceutical Co., Ltd., Osaka, Japan

[21] Appl. No.: 154,730

[22] Filed: Nov. 18, 1993

Related U.S. Application Data

[63] Continuation of Ser. No. 805,624, Dec. 12, 1991, abandoned.

[30] Foreign Application Priority Data

Dec. 21, 1990 [JP] Japan ..................................... 2-418298

[51] Int. Cl.$^6$ ..................................................... A61K 38/12
[52] U.S. Cl. ................................. 514/11; 514/9; 514/16; 514/826; 530/317; 530/323; 530/329; 530/345
[58] Field of Search ........................... 514/9.11, 16, 826; 530/3, 7, 323, 329, 345

[56] References Cited

U.S. PATENT DOCUMENTS 5,093,127  3/1992  Asakura et al. .................. 424/434
5,164,374  11/1992  Matsuo et al. .................... 514/19

FOREIGN PATENT DOCUMENTS 0336230  10/1989  European Pat. Off. .
0394989A2  10/1990  European Pat. Off. .
0400637  12/1990  European Pat. Off. .

OTHER PUBLICATIONS

European Official Action Dated Aug. 27, 1993.
The Merck Manual of Diagnosis and Therapy, 11th ed., pp. 948–953 (1966).

*Primary Examiner*—Christina Y. Chan
*Assistant Examiner*—T. D. Wessendorf
*Attorney, Agent, or Firm*—Oblon, Spivak, McClelland, Maier & Neustadt, P.C.

[57] ABSTRACT

Rheumatoid arthritis and osteoarthrosis are treated by administering an effective amount of tetrahydro-WS9326A to a human being or animal suffering from rheumatoid arthritis or osteoarthrosis.

3 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: both ( i i ) MOLECULE TYPE: peptide ( x i ) SEQUENCE DESCRIPTION: SEQ ID NO:1:

Xaa  Xaa  Leu  Phe  Xaa  Asn  Xaa
    1                          5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:2:

Xaa  Xaa  Leu  Phe  Thr  Asn  Ser
    1                         5

METHOD OF TREATING RHEUMATOID ARTHRITIS AND OSTEOARTHROSIS USING TETRAHYDRO WS9326A

This application is a Continuation of application Ser. No. 07/805,624, filed on Dec. 12, 1991 now abandoned.

This invention relates to an antiinflammatory or gastrointestinal motility-modulating composition comprising a peptide derivative of the general formula (I) presented hereafter or a pharmaceutically acceptable salt thereof as an active ingredient, which composition finds application in the field of medicine.

The peptide derivative of the invention, represented by the general formula (I) given below, is a per se known compound and is known to possess pharmacological activities such as substance P antagonism and neurokinin A antagonism (e.g. EP 0336230A2). However, there has not been the awareness that this peptide derivative has antiinflammatory or gastrointestinal motility-modulating activity.

This invention relates to an antiinflammatory or gastrointestinal motility-modulating composition characterized by comprising a peptide derivative of the general formula (SEQ ID NO: 1):

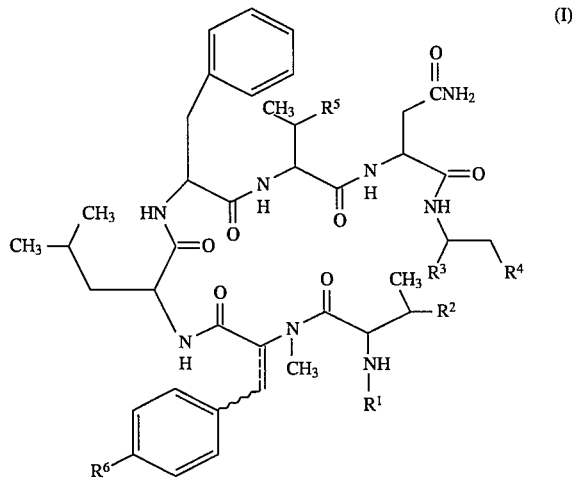

(I)

wherein
$R^1$ is hydrogen or an acyl group;
$R^2$ is hydroxy and
$R^3$ is carboxy or protected carboxy, or
$R^2$ and $R^3$ are linked together to represent a group of the formula:

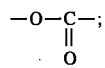

$R^4$ is hydroxy or protected hydroxy;
$R^5$ is hydroxy or protected hydroxy;
$R^6$ is hydroxy, protected hydroxy or lower alkoxy; and
═ is a single bond or a double bond, or a pharmaceutically acceptable salt thereof as an active ingredient.

Suitable pharmaceutically acceptable salts of the compound (I) are conventional non-toxic salts and may. include a salt with a base or an acid addition salt such as a salt with an inorganic base, for example, an alkali metal salt (e.g. lithium salt, sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.) and the like.

In the above and subsequent description of the present specification, suitable examples and illustration of the various definitions which the present invention include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated. Suitable "acyl" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Alliphatic acyl such as lower or higher alkanoyl (e.g. formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.);

lower or higher alkoxysulfonyl (e.g. methoxysulfonyl, ethoxysulfonyl, etc.); or the like;

Aromatic acyl such as aroyl (e.g. benzoyl, toluoyl, naphthoyl, etc.);

ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g. naphthylacetyl, naphthylpropanoyl, naphthylbutanoyl, etc.), etc.];

ar(lower)alkenoyl [e.g. phenyl(lower)alkenoyl (e.g. phenylpropenoyl, phenylbutenoyl, phenylmethacryloyl, phenylpentenoyl, phenylhexenoyl, etc.), naphthyl(lower)alkenoyl (e.g. naphthylpropenoyl, naphthylbutenoyl, naphthylpentenoyl, etc.), etc.];

ar(lower)alkoxycarbonyl [e.g. phenyl(lower)alkoxycarbonyl (e.g. benzyloxycarbonyl, etc.), etc.];

aryloxycarbonyl (e.g. phenoxycarbonyl, naphthyloxycarbonyl, etc.);

aryloxy(lower)alkanoyl (e.g. phenoxyacetyl, phenoxypropionyl, etc.);

arylglyoxyloyl (e.g. phenylglyoxyloyl, naphthylglyoxyloyl, etc.);

arylsulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.);

heterocyclic (lower)alkanoyl (e.g. thienylacetyl, thienylpropanoyl, thienylbutanoyl, thienylpentanoyl, thienylhexanoyl, thiazolylacetyl, thiadiazolylacetyl, tetrazolylacetyl, etc.);

heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl"0 and "heterocyclicglyoxyloyl" as mentioned above means, in more detail, saturated or unsaturated, monocyclic or polycyclic heterocyclic group containing at least one heteroatom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered)heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered (more preferably 5 or 6-membered)heteromonocyclic group containing 1 to 2 oxygen atom(s) and 1 to 3 nitrogen atom(s), for example, oxazoly1, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered (more preferably 5 or 6-membered)heteromonocyclic group containing 1 to 2 oxygen atom(s) and 1 to 3 nitrogen atom(s), for example, morpholinyl, sydnonyl etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, etc.;

unsaturated condensed heterocyclic group containing 1 to 2 sulfur atom(s) and 1 t,D 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The acyl moiety as stated above may have one to ten, same or different, suitable substituent[s] such as lower alkyl (e.g methyl, ethyl, propyl, isopropyl, butyl, isobutyl, t-butyl, pentyl, hexyl, etc.);

lower alkenyl (e.g. vinyl, allyl, 1-propenyl, 1 or 2 or 3-butenyl, 1 or 2 or 3 or 4-pentenyl, 1 or 2 or 3 or 4 or 5-hexenyl, etc.);

lower alkoxy (e.g. methoxy, ethoxy, propoxy, etc.);

lower alkylthio (e.g. methylthio, ethylthio, etc.);

lower alkylamino (e.g. methylamino, etc.);

cyclo(lower)alkyl (e.g. cyclopentyl, cyclohexyl, etc.);

cyclo(lower)alkenyl (e.g. cyclohexenyl, etc.); halogen; amino; protected amino; hydroxy; protected hydroxy; cyano; nitro; carboxy; protected carboxy; sulfo; sulfamoyl; imino; oxo;

amino(lower)alkyl (e.g. aminomethyl, aminoethyl, etc.); carbamoyloxy; hydroxy (lower)alkyl (e.g. hydroxymethyl, 1 or 2-hydroxyethyl, 1 or 5 or 3-hydroxypropyl, etc.); cyano(lower)alkenylthio (e.g. cyanovinylthio, etc.); or the like.

Suitable "hydroxy protective group" in the term "protected hydroxy" may include phenyl (lower)alkyl (e.g. benzyl, etc.), acyl as mentioned above, and the like. Suitable "carboxy " may include esterified carboxy.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1 (or 2)-isobutyryloxyethyl ester, 1 (or 2)-pivaloyloxyethyl ester, 1 (or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g.

2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.);

ar(lower)alkyl ester which may have at least one suitable substituent(s) such as mono(or di or tri)phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.);

phthalidyl ester; and the like.
suitable "lower alkoxy" may include methoxy, ethoxy, propoxy, isopropoxy, butoxy, isobutoxy, t-butoxy, pentyloxy, hexyloxy and the like. Suitable "amino protective group" in the term "protected amino" may include acyl as mentioned above, and the like.

Preferable embodiments of the compound (I) are as follows.

$R^1$ is hydrogen, ar(lower)alkoxycarbonyl (more preferably phenyl(lower)alkoxycarbonyl), lower alkanoyl, higher alkanoyl (more preferably $C_{15}$–$C_{20}$ alkanoyl), aroyl (more preferably benzoyl), heterocyclic(lower)alkanoyl (more preferably thienyl(lower)alkanoyl), ar(lower)alkenoyl substituted with a lower alkenyl group (more preferably phenyl(lower)alkenoyl substituted with a lower alkenyl group), or ar(lower)alkanoyl substituted with a lower alkyl group (more preferably phenyl(lower)alkanoyl substituted with a lower alkyl group);

$R^2$ is hydroxy and $R^3$ is carboxy or esterified carboxy (more preferably lower alkoxycarbonyl), or $R^2$ and $R^3$ are linked together to represent a group of the formula:

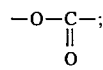

$R^4$ is hydroxy, ar(lower)alkoxy (more preferably phenyl(lower)alkoxy) or acyloxy (more preferably lower alkanoyloxy);

$R^5$ is hydroxy, ar(lower)alkoxy (more preferably phenyl(lower)alkoxy) or acyloxy (more preferably lower alkanoyloxy);

$R^6$ is hydroxy, lower alkoxy, ar(lower)alkoxy (more preferably phenyl1 (lower)alkoxy) or acyloxy (more preferably lower alkanoyloxy); and ═══ is a single bond or a double bond.

The compound (I) or a pharmaceutically acceptable salt thereof, in accordance with the invention, has antiinflammatory and gastrointestinal motility-modulating activities and, as such, is of value as an active ingredient for use in antiinflammatory or gastrointestinal motility-modulating compositions.

The antiinflammatory composition of this invention is effective in preventing and treating inflammation such as various types of arthritis [e.g. articular rheumatism (e.g. rheumatoid arthritis, etc.), osteoarthrosis (e.g. osteoarthrosis of knee, etc.), periarthritis humeroscapularis, cervico-omobrachial syndrome, etc.] or the like, and the gastrointestinal motility-modulating composition of this invention is effective in modulating the gastrointestinal motility and therefore effective in preventing and treating irritable bowel syndrome [e.g. diarrhea, constipation, etc.], and the like.

The compound (I) or a pharmaceutically acceptable salt thereof, which is used as an active ingredient of said compositions, can be administered as it is but is generally administered in the form of a pharmaceutically acceptable preparation.

The pharmaceutical preparation mentioned above may take a variety of forms such as oral preparation [e.g. solution, emulsion, suspension, capsule, granule, powder, tablet, syrup, etc.], injection, suppository or the like.

Such preparations can be manufactured by the established pharmaceutical procedures using appropriate excipients such as sucrose, starch, mannitol, sorbitol, lactose, glucose, cellulose, talc, calcium phosphate, calcium carbonate, etc.; binders such as cellulose, methylcellulose, hydroxypropylcellulose, polypropylpyrrolidone, gelatin, gum arabic, polyethylene glycol, sucrose, starch, etc.; disintegrators such as starch, carboxymethylcellulose, hydroxypropyl starch, sodium bicarbonate, calcium phosphate, calcium citrate, etc.; lubricants such as magnesium stearate, talc, sodium laurylsulfate, etc.; corrigents such as citric acid, menthol, glycine, orange powder, etc.; preservatives such as sodium benzoate, sodium bisulfite, benzyl alcohol, methylparaben, propylparaben, etc., stabilizers such as citric acid, sodium citrate, acetic acid, etc.; suspending agents such as methylcellulose, polyvinylpyrrolidone, aluminum stearate, etc.; dispersants such as hydroxypropylmethylcellulose, polysorbate 80, carboxymethylcellulose, etc.; solvents such as water, etc.; isotonicity such as sodium chloride, etc.; base waxes such as cacao butter, polyethylene glycol, white soft paraffine, etc.; and so on.

The dosage for the pharmaceutical composition of this invention depends on the patient's human being or animal age, body weight and clinical condition, the method of administration and other conditions. Generally speaking, however, the active compound (I) or a pharmaceutically acceptable salt thereof is administered in doses of 1 to 300 mg and preferably 10 to 100 mg, either orally or parenterally (for examples intraarticularly, intravenously).

The following test example are intended to demonstrate the excellent antiinflammatory and gastrointestinal motility-modulating actions of the present compound (I) or a pharmaceutically acceptable salt thereof.

Test compound
The compound of the following structural formula (SEQ ID NO: 2):

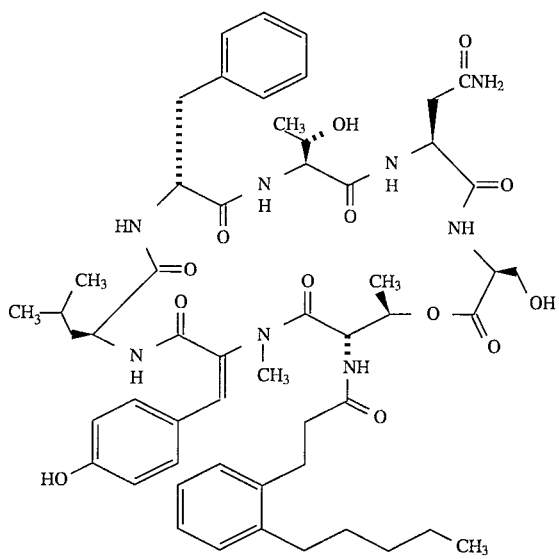

(hereinafter referred to briefly as tetrahydro-WS9326A)

(a) Effect on carrageenin-induced rat knee edema:

Eight-week-old male Wistar rats were used.

Each rat was anesthetized with 0.2 ml of pentobarbital sodium (50 mg/ml) in physiological saline i.p. and then intravenously dosed with 2 ml/kg of Evans blue (10 mg/ml) in physiological saline. Thereafter, 0.1 ml of 2% carrageenin in physiological saline was administered into the articular cavity of the right knee. After 4 hours, the animal was sacrificed, skinned to expose the articular region and observed for leakage of Evans blue. Then, physiological saline (0.15 ml) was injected into the articular cavity. After incision, 5 μl of synovial fluid was collected. The synovial fluid obtained was diluted with physiological saline (40 μl) and using a cell counter, the cells were counted under the microscope.

The test compound (tetrahydro-WS9326A) was suspended in 0.1% methylcellulose in physiological saline and 0.1 ml of this suspension was administered into the knee joint 15 minutes before carrageenin administration.

| | Test results | | |
|---|---|---|---|
| Dose | No. of animals | No. of cells in synovial fluid ($\times 10^4$/ml) | % Inhibition |
| vehicle (0.1% methyl cellulose in physiologial saline) only | 5 | 675.2 ± 105.7 | — |
| 1 μg | 5 | 543.2 ± 135.1 | 19.5 |
| 10 μg | 5 | 302.8 ± 77.1 | 55.2 |
| 100 μg | 5 | 60.8 ± 11.8 | 91.0 |

(b) Effect on charcoal transport in mice:

Five-week-old male ICR mice, fasted overnight, were used. The test compound (tetrahydro-WS9326A) was dissolved in a solvent [ethanol-polyethylene glycol 400-distilled water (1:1:3)] and the resulting solution (0.1 ml/10 g) was administered intraperitoneally. After 10 minutes, a 10% suspension (0.1 ml/20 g) of charcoal in castor oil or a 10% suspension (0.1 ml/20 g) of charcoal in 0.5% methylcellulose—physiological saline was administered orally. Twenty minutes later, the mice were killed, the small intestine was excised and the distance traversed by the charcoal was measured.

| | Test results | | |
|---|---|---|---|
| Dose (mg/kg) | Charcoal | No. of animals | % Transport* |
| Vehicle only | Charcoal/0.5% methylcellulose in physiological saline | 10 | 56.9 ± 3.9 |
| vehicle only | Charcoal/castor oil | 10 | 70.5 ± 2.9 |
| 1 | Charcoal/castor oil | 10 | 66.9 ± 3.0 |
| 10 | Charcoal/castor oil | 10 | 51.3 ± 1.9 |

*% Transport = $\dfrac{\text{Distance traversed by charcoal}}{\text{Length of small intestine}} \times 100$ (c) Toxicity study An injectable suspension containing the test compound and other ingredients mentioned below was administered into the knee joint of rabbits (6 males and 6 females) and dogs (3 males and 3 females) twice a week for 4 weeks. The dose was 8 mg/kg for rabbits and 12 mg/kg for dogs. The administration of the test compound caused death in neither rabbits nor dogs.

| [Injectable suspension (ingredients per milliliter)] | |
|---|---|
| Tetrahydro-WS9326A | 20 mg |
| Polysorbate 80 | 2 mg |
| Carboxymethylcellulose sodium | 7.5 mg |
| Benzyl alcohol | 9 mg |
| Sodium chloride | 9 mg |
| Distilled water for injection | q.s. |

The following examples are illustrative of the invention.

EXAMPLE 1

A powder of the following composition is encapsulated to provide capsules.

| Formula | |
|---|---|
| Tetrahydro-WS9326A | 100 mg |
| Low-substituted hydroxypropylcellulose | 10 mg |
| Polyoxyl 40 stearate | 1 mg |
| Hydroxypropylcellulose | 1 mg |

EXAMPLE 2

The following ingredients are admixed and granulated in the routine manner to provide granules.

| Formula for granules | |
|---|---|
| Tetrahydro-WS9326A | 30.0 (wt. %) |
| Lactose | 69.4 |
| Polyoxyl 40 stearate | 0.1 |
| Hydroxypropylcellulose | 0.5 |

EXAMPLE 3

The following ingredients are admixed and powdered in the routine manner to provide a powder.

| Formula for powder | |
| --- | --- |
| Tetrahydro-WS9326A | 30.0 (wt. %) |
| Lactose | 69.4 |
| Polyoxyl 40 stearate | 0.1 |
| Hydroxypropylcellulose | 0.5 |

EXAMPLE 4

The following ingredients are admixed and compressed in the routine manner to provide tablets.

| Formula for tablets | |
| --- | --- |
| Tetrahydro-WS9326A | 300 (mg) |
| Lactose | 100.8 |
| Croscarmellose sodium, type A | 9 |
| Hydroxypropylcellulose | 3 |
| Polyoxyl 40 stearate | 3 |
| Magnesium stearate | 4.2 |
| | 420 mg/tablet |

Where necessary, the tablets thus obtained are film-coated or enteric-coated to provide film coated or enteric coated tablets.

EXAMPLE 5

To 100 ml of distilled water for injection is added 1 g of carboxymethylcellulose sodium and the mixture is stirred. To the resulting solution is added 40 mg of Polysorbate 80 and, after mixing, 1 g of tetrahydro-WS9326A is dispersed therein to provide an injectable suspension.

EXAMPLE 6

To 50 ml of macrogol 400 is added 1 g of tetrahydro-WS9326A and the mixture is stirred. The resulting solution is made up to 100 ml with distilled water for injection to provide an injectable solution.

EXAMPLE 7

After tetrahydro-WS9326A is dispersed in a solution of Polysorbate 80 in distilled water for injection, a solution of sodium chloride, benzyl alcohol and carboxymethylcellulose sodium in distilled water for injection is added thereto. 5 Ml of the resulting suspension is filled into an ampoule, which is then sealed by fusion to provide an injectable suspension containing the following ingredients.

| Ingredients (per milliliter) | |
| --- | --- |
| Tetrahydro-WS9326A | 10 mg |
| Polysorbate 80 | 2 mg |
| Carboxymethylcellulose sodium | 7.5 mg |
| Benzyl alcohol | 9 mg |
| Sodium chloride | 9 mg |
| Distilled water for injection | q.s. |

Tetrahydro-WS9326A was obtained by subjecting the compound of the above structural formula (SEQ ID NO: 2) to reduction with 10% Pd-C.

What we claim is:

1. A method for treating rheumatoid arthritis or osteoarthrosis, comprising:

administering an effective amount of the peptide having the formula (SEQ ID No. 2):

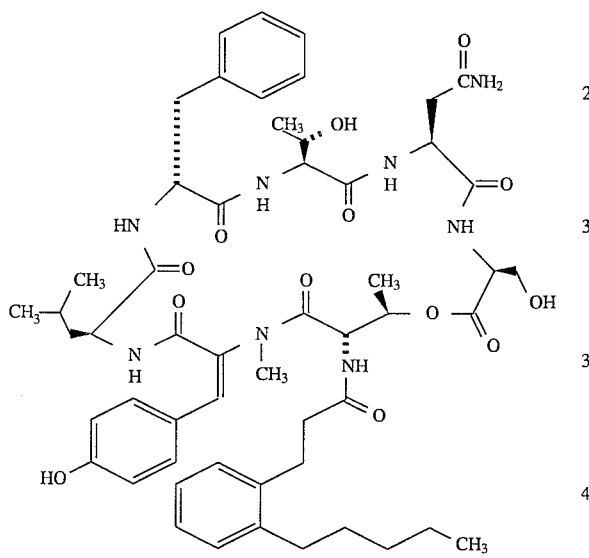

or a pharmaceutically acceptable salt thereof to a human being or animal suffering from said rheumatoid arthritis or osteoarthrosis.

2. The method of claim 1, wherein said peptide is administered parenterally in an amount of from 1 to 300 mg.

3. The method of claim 2, wherein said amount is from 10 to 100 mg.

* * * * *